United States Patent [19]
Celebuski

[11] Patent Number: 5,932,413
[45] Date of Patent: Aug. 3, 1999

[54] DNA PROBE ASSAY USING NEUTRALLY CHARGED PROBE STRANDS

[76] Inventor: Joseph Eugene Celebuski, 5080 Fox La., Gurnee, Ill. 60031

[21] Appl. No.: 07/672,157

[22] Filed: Mar. 19, 1991

Related U.S. Application Data

[63] Continuation of application No. 07/176,517, Apr. 1, 1988, abandoned.
[51] Int. Cl.⁶ .............................. C12Q 1/68; C07H 21/04
[52] U.S. Cl. ................................................ 435/6; 536/24.3
[58] Field of Search ................................... 435/6; 536/27, 536/24.3; 935/77, 78

[56] References Cited

U.S. PATENT DOCUMENTS

| | | | |
|---|---|---|---|
| 4,302,204 | 11/1981 | Wan et al. | 435/6 |
| 4,469,863 | 9/1984 | Ts'o et al. | 536/24.5 |

OTHER PUBLICATIONS

Marchionni et al. (Marchionni), *Journal of Virology*, vol. 38, No. 1, pp. 294–304 (1981).
Zwadyk et al. (Zwadyk), *CRC Critical Reviews in Clinical Laboratory Sciences*, vol. 25, No. 1, pp. 73–103 (1987).
Bernardi, *Nature*, vol. 206 (1965) pp. 779–783.
Aebersold, et al., *The Journal of Biological Chemistry*, 261(9):4229–4238 (Mar. 25, 1986).
Blake, et al., *Biochemistry*, 24:6139–6145 (1985).
Hewick, et al., *The Journal of Biological Chemistry*, 256(15):7990–7997 (Aug. 10, 1981).
Jayaraman, et al., *Proc. Natl. Acad. Sci. USA*, 78(3):1537–1541 (Mar. 1981).
Lesnikowski, et al., *Tetrahedron Letters*, 28(45):5535–5538 (1987).
Miller, et al., *Biochemistry*, 25:5092–5097 (1986).
Murakami, et al., *Biochemistry*, 24:4041–4046 (1985).
Renz, et al., *Nucleic Acids Research*, 12(8):3435–3444 (1984).
Smith, et al., *Proc. Natl. Acad. Sci. USA*, 83:2787–2791 (May 1986).
Stirchak, et al., *J. Org. Chem.*, 52(19):4202–4206 (Sep. 18, 1987).
Applied Biosystems Nucleic Acid Research News, Issue No. 3 (Jul. 20, 1987).
Applied Biosystems Brochure, Issue No. 43 (Aug. 20, 1987).
Bower, et al., Applied Biosystems Brochure, pp. 1–4 (1987).

*Primary Examiner*—David Guzo
*Attorney, Agent, or Firm*—Thomas D. Brainard; Paul D. Yasger

[57] ABSTRACT

A DNA probe assay is described using neutrally charged probe strands.

29 Claims, 1 Drawing Sheet

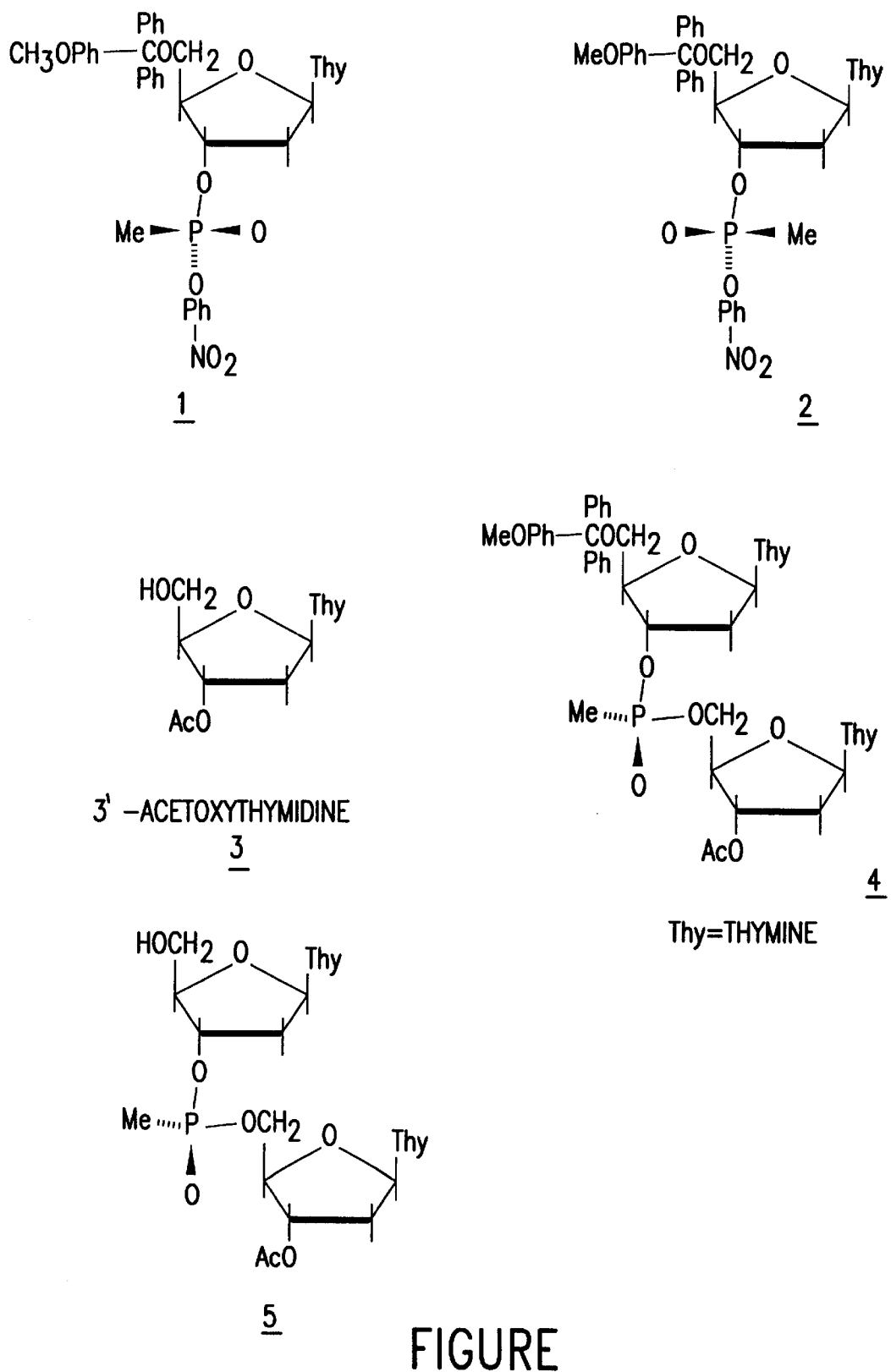
FIGURE

DNA PROBE ASSAY USING NEUTRALLY CHARGED PROBE STRANDS

This application is a Continuation of application Ser. No. 07/176,517, filed Apr. 1, 1988, now abanboned.

BACKGROUND

The present invention relates to assays using labeled probe strands with DNA complementary to strands of DNA in a sample to detect the presence of the DNA in the sample by analyzing for the labeled probe strands.

DNA probe assays typically involve analyzing for one or more copies of a first strand of oligonucleotides in a sample by introducing plural second strands of oligonucleotides which are complementary to the first strand(s), so as to hybridize to the first strands if first strands are in the sample. Second strands are labeled (e.g. with phosphorus-32, chemiluminescent compounds such as acridines and luminols, fluorescent compounds such as fluorescein and rhodamine, biotin, and enzymes such as alkaline phosphatase and acid phosphatase, and liposomes containing such labels) so they can be detected in the sample.

One problem in the past with DNA probe assays is in separating the hybridized probe strands from the unhybridized probe strands. A separation system based upon size differences between probe, target, and probe-target duplex works, but the methods used are tedious and difficult to automate. As an example, a Southern blot assay [Southern, *Journal Molecular Biology*, 98:503–517 (1975)] is difficult to automate. Another assay which utilizes size separation is the Abbott Laboratories "Genostics" assay for hepatitis B virus. In the "Genostics" assay, native HB DNA is hybridized to iodine-125 labelled probe. The DNA-probe hybrid is then passed through a size exclusion column with enough volume of eluent to give only the hybrid in solution in a collection flask. The flask is then assayed for radio-isotope by standard methods. Although this method works well, a technician still must run the test. The method, then, is also not amenable to automation. Few satisfactory solutions to the separation problem in automated systems have been proposed.

SUMMARY OF THE INVENTION

The DNA probe assay for this invention provides probe strands which afford easy separation of the hybridized from the unhybridized probe strands. With an appropriate label, therefore, the DNA probe assay of this invention can readily be adapted to be performed using automated equipment.

The assay of this invention can detect a first oligonucleotide sequence in a sample by introducing into the sample a second probe oligonucleotide sequence complementary to the first oligonucleotide sequence. The second oligonucleotide sequence is composed of neutrally charged nucleotides, so that the first and second sequence hybridize. Any unhybridized probe strands can be separated from the hybridized probe strands simply by contacting the sample with a positively charged solid phase, followed by a wash. The first oligonucleotide sequence contains an intrinsic negative charge due to the P=O moiety in each of the nucleotides which comprise the first oligonucleotide strand in the sample. The negative moieties will be retained on the positively charged solid phase, thus retaining the hybridized probe strand on the solid phase as well. The unhybridized, neutrally charged probe strand, will not be retained by the solid phase. Accordingly, with an appropriate label on the probe strand, the amount or presence of the first oligonucleotide sequence in the sample can be analyzed by assaying the solid phase or the unhybridized probe strands for the presence of the label.

In one embodiment of this invention, the probe strands are rendered neutrally charged by synthesizing the probe strand from alkyl phosphonate nucleotides, thus eliminating the charged P=O moiety from the probe strand. Preferably, the alkyl phosphonate nucleotides are chirally resolved to use substantially only the R stereoisomers of each nucleotide. It has been found that mixtures of R and S stereoisomers (a racemic mixture) will not hybridize to the first oligonuceotide sequence in the sample quite as well as the chirally resolved probe strands will.

BRIEF DESCRIPTION OF THE DRAWING

The FIGURE illustrates several compounds made in accordance with the present invention.

DETAILED DESCRIPTION OF THE INVENTION

This invention involves the use of neutrally charged DNA probe strands in a DNA probe assay where the probe strands hybridize to an oligonucleotide sequence in a sample to be tested. DNA in samples of blood, bacteria, or other bodily fluids normally is composed of nucleotides having a charged P=O grouping, imparting an overall negative charge to the DNA strand and sample. When the uncharged probe strand hybridizes with the charged oligonucleotide sequence in the sample, the hybridized DNA strand also has an overall negative charge. Thus, the hybridized strands can be separated from the unhybridized probe strands by contacting the sample containing both hybridized and unhybridized probe strands with a positively charged solid phase. The negatively charged hybridized strands will collect on the positively charged solid phase, but the uncharged, unhybridized probe strands will not. It is a simple matter with techniques known in the art to separate the solid phase containing the hybridized probe strands from the liquid phase containing the unhybridized probe strands, and the presence or quantity of the oligonucleotide sequence to be determined in the sample can be ascertained either by measuring the amount of hybridized probe strand on the solid phase or by measuring the unhybridized probe strand in the liquid phase. In the preferred embodiment of this invention, proteinase K is added to the sample which contains the target DNA before the probe strands are introduced, in order to hydrolyze proteins which might be present.

Neutrally Charged Oligonucleotides

The neutrally charged oligonucleotides used in this invention are preferably alkyl phosphonate nucleotides which replace the normal P=O negatively charged moiety in the bases with an alkylated phosphonate group. The alkylphosphonates which can be used include methylphosphonate, ethylphosphonate, methylthiophosphonate, and methoxyphosphonate. The nucleotides to which the above alkylphosphonates can be appended at the 3' position include thymidine, guanidine, adenosine, cytidine, and 5-aminoallyluridine.

In using alkylated phosphonate nucleotides to render the probe strand "neutrally charged," it is not necessary to synthesize the probe strands from 100% alkyl phosphonate nucleotides. As long as the probe strand is synthesized from a sufficient percentage of "neutrally charged" nucleotides that the unhybridized probe strands either will pass through or can be washed off the positively charged solid phase while the hybridized probe strands remain with the solid phase, the probe strand can be considered "substantially neutrally charged" within the scope of this invention. It is believed that the probe strand should contain at least about 75 percent of neutrally charged nucleotides.

It has been found that in synthesizing alkylated phosphonate nucleotides that a chiral center is created on each phosphorus. It is preferable to resolve the R and S stereoisomers of the nucleotides from each other, and synthesize the probe strands only from the R stereoisomer nucleotides. It has been found that the R stereoisomer nucleotides hybridize more readily to the target oligonucleotide sequences in the sample than probe strands made from S stereoisomers or from racemates. The separation of R from S steroisomers is described in Example 1 below. Other methods which can be used to produce neutrally charged oligonucleotides include preparing chirally resolved alpha-P-alkyl nucleotide triphosphates for the four major nucleotide triphosphates, and then enzymatically incorporating these bases into a probe using DNA polymerases.

Solid Phases

The present invention utilizes solid phase materials which are positively charged. The solid phase material can be chosen for its intrinsic ability to attract the negatively charged hybridized probe strands, for example, methylated wool, nylons and certain glasses have intrinsic positive charges. Alternatively, a positively charged substance can be coated on or conjugated to the solid phase material. The solid phase material can include virtually any of the porous materials known to those skilled in the art, through which materials fluids can flow and easily pass. For example, the solid phase material can include 1) fiberglass, cellulose, or nylon pads for use in a flow through assay device having one or more layers containing one or more assay reagents; 2) a dipstick for a dip and read assay; or 3) a strip for chromatographic (e.g. paper) or thin layer of chromatographic (e.g. nitrocellulose) techniques in which one or all of the reagents are contained in separate zones of a single strip of solid phase material. The solid phase material, however, is not limited to porous material. The solid phase material can include beads, magnetic beads, latex particles, a glass test tube or any other material which has an intrinsic positive charge or which can retain a positively charged substance.

Natural, synthetic, or naturally occurring materials that are synthetically modified can be used as a solid phase material. Such materials include polysaccharides, e.g. cellulose materials such as paper and cellulose derivatives including cellulose acetate and nitrocellulose; silica; inorganic materials such as deactivated alumina, diatomaceous earth, magnesium sulfate, or other inorganic finely divided material uniformly dispersed in a porous polymer matrix, with a polymer such as vinyl chloride, vinyl chloride propylene copolymer, and vinyl choride-vinyl acetate copolymer, cloth, both naturally occurring (e.g. cotton) and synthetic (e.g. nylon); gels such as silica gel, agarose, dextran and gelatin; polymeric films such as polyacrylamide; and the like.

Preferred solid phase materials include porous fiberglass materials such as a Whatman 934-AH filter paper which has a nominal thickness of 0.33 mm or other fiber matrix devices. The thickness of the material is not critical and will be a matter of choice, largely based on the properties of sample or analyte being assayed such as the fluidity of the test sample.

To change or enhance the intrinsic charge of the solid phase material, a positively charged substance can be coated directly to the material or onto microparticles which have been retained by a solid phase material. Alternatively, microparticles alone can be used as the charged solid phase material. One possible charged substance is a polymeric cation which is retained by the solid phase material and will retract and retain the negatively charged hybridized probe strands via the attraction of opposite charges. A wide variety of proprietary polycations are available including quaternary ammonium salts such as "GAFQUAT", (GAF Corporation, Wayne, N.J. 07470), "CELQUAT" L-200 and "CELQUAT" H-100 (National Starch and Chemical Corporation, Bridgewater, N.J. 08807).

The charged substance can be coated on the particles (e.g. beads or microparticles). These particles serve as solid phase by being retained in a column or being suspended in a mixture of soluble reagents and test sample, or the particles themselves can be retained and immobilized by a solid phase material. By "retained and immobilized" it is meant that the particles that are on the solid phased material are not capable of substantial movement to positions elsewhere within the material. These particles can be selected by one skilled in the art from any suitable type of particulate material composed of polystyrene, polymethylacrylate, polypropylene, latex, polytetrafluoroethylene, polyacrylnitrile, polycarbonate, or similar materials. The size of the particles is not critical, although we prefer that the average diameter of the particles be smaller than the average pore size of the solid phase material being used.

EXAMPLES

The following examples illustrate the preferred ways of performing DNA probe assays according to the present invention. The examples, however, are intended only to be illustrative and are not to be construed as placing limitations on the scope of the invention, which scope is defined solely by the pending claims.

Example 1

Enantiomerically pure 3'-methylphosphonate substituted nucleotides were prepared by the method of Lesnikowski, Wolkanin, and Stec, *Tetrahedron Letters* 28 5535-8 (1987). The procedure for the synthesis of 1 and 2, the Sp and Rp enantiomers of 5'-O-monomethoxytritylthymidine-3'-0-(O-(4-nitrophenyl) methanephosphonate) is as follows. The 5'-MMT-N-4-benzoyladenosine, 5'-MMT-N-4-benzoylcytidine, and 5'-MMT-N-2-isobutylguanidine methylphosphonate derivatives were prepared similarly. To a solution of MeP(O)Cl$_2$ (200 mg) in pyridine (6 mL) under an argon atmosphere in a flame-dried flask was added a solution of 5'-0-monomethoxytritylthymidine (257.7 mg) in pyridine (3 mL) at room temperature over the course of 45 minutes. The mixture was stirred upon completion of addition for one hour longer, then 4-nitrophenol (627 mg) was added all at once. After being stirred for one hour, the reaction was quenched with 50% aqueous pyridine (2 mL). After the addition of saturated NaHCO$_3$ (90 mL), the emulsion was extracted 2×100 mL CHCl$_3$. The chloroform extracts were dried over MgSO$_4$, filtered, evaporated, and vacuum dried. The residue was dissolved into 1% MeOH in CHCl$_3$ (6 mL), and the solution was applied to a flash chromatography column packed in the same solvent. The compounds were eluted using a 1–8% gradient of MeOH in CHCl$_3$. The UV active spots which had $R_f$s of 0.6 and 0.53 in 95:5 CHCl$_3$: MeOH on silica gel gave 85.9 mg of compound 1 (shown in the attached FIGURE) and 91 mg of 2 (see the FIGURE), respectively.

Example 2

The enantiomerically pure 2 prepared in Example 1 was condensed with 3'-acetoxythymidine 3 in the same manner cited by Lesnikowski, Wolkanin, and Stec. (supra) as follows. The oligomer, 5'-TT*T*T*T*T-3', where the asterisk signifies an enantiomerically pure 3' to 5' methylphosphonate linkage, was prepared by a stepwise process involving successive condensations of 2 onto the growing oligonucleotide chain in the 5' direction. The final condensation to afford the normal phosphodiester linkage was accomplished with 5'-acetoxythymidine-3'-phosphate, DCC, and tetrazole. To a solution of 3'-acetoxythymidine (16.6 mg) in THF (7 mL) under an argon atmosphere at 0° C. was added 2.0M t-BuMgCl in THF (30 uL) via syringe. Within 15 minutes, a white precipitate appeared. The suspension was stirred at 0° C. for 30 minutes longer, then compound 2 (32 mg) dissolved in THF (3 mL) was added. The mixture was stirred at room temperature for one hour, then DMF (100 uL) was added. The mixture was stirred for a total of 19 hours. The solvents were removed in vacuo, and the residue was vacuum dried. The material was taken up into 0.8% MeOH in $CHCl_3$. Flash Chromatography of the material was done using a stepwise gradient of 250 mL each of 0.8%, 2%, 4%, 6%, and 8% MeOH in $CHCl_3$. The product 4 eluted in 6% MeOH in $CHCl_3$, and possessed an $R_f$ of 0.32 in 95:5 $CHCl_3$ MeOH. The monomethoxytrityl group was removed from the 5' end of the adduct using 2% toluenesulfonic acid in 7:3 $CHCl_3$: MeOH to give 5. Compound 5 was then used to elongate the chain, deprotonating the 5'-OH with t-BuMgCl and reacting the resultant anion with another equivalent of 2.

Example 3

The cationic quat coating protocol for fiberglass filter discs, used for the ion capture assay described in Example 4, is detailed below. Each of ten Whatman fine fiberglass filter discs (2.5 cm ID) were soaked in 10 mL of a 25 mg/mL solution of Celquat L-200 (National Starch & Chemical Corp., Batch # 10, date of manufacture May 3, 1982) in water for two and one-half hours. Then, the Celquat solution was decanted, and each disc was washed with 10×20 mL distilled water. To test the efficacy of anionic capture using these cationic filters, the following control experiment was run. A sample (0.5 pmol) of the 16-mer M13 hybridization probe primer 5'-dCACAATTCCACACAAC-3° (New England Biolabs #1202, lot 14–15) was kinased with T4 polynucleotide kinase and γ-$^{32}$P ATP (2.5 pmol). The radioactive DNA was diluted to 500 uL, and was applied in triplicate aliquots to six 1 cm ID filter discs. Three discs were quat treated with Celquat L-200, while the other three discs were not treated with guat. The discs were washed with 1 mL of 100 mM NaCl/10 mM tris/1 mM EDTA pH 8.0 buffer (STE). The filters were assayed for radioactivity in a scintillation counter. The quat treated filters retained 71% of the total radioactive counts, while the control filters retained 7% of the radioactive counts. Thus, the cationic quat treated fiberglass filters trap and retain polyanions such as DNA, in preference to non-quat treated fiberglass filters. Thus, DNA can be assayed for using this ionic capture format.

Example 4

The oligomer 3, 5'-TT*T*T*T*T-3', where T* indicates a MeP(O) linkage of R stereochemistry from 3' to 5', was treated with T4 polynucleotide kinase and γ-$^{32}$P ATP in order to label the 5' terminus of the oligonucleotide with $^{32}$p. The end-labeled probe 3 was then hybridized to pd(A)$_{20}$ (Pharmacia, lot #00088472) at 55° C. for one hour. When the duplex was applied to a quat-treated filter disc from Example 3, and washed with STE buffer (1 mL), most of the radioactive counts stayed on the filter disc, as seen by scintillation counting. This showed that hybridization occurred. Thus, a labeled neutral probe can be detected in this assay configuration, essentially using the target DNA to bind the neutral probe to the filter. In the control experiment, oligomer 3 was kinased with γ-$^{32}$P- ATP and T4 polynucleotide kinase, and the radioactive probe was applied to quat-treated filter discs. Fewer than 1% of the total radioactive counts emanating from the labeled neutral probe could be detected on the filter disc after a 1 mL STE wash.

Example 5

A synthesis and purification scheme for a racemic methylphosphonate neutral probe is described in this example. The complementary for M13 17-mer GT*C*A*T*A*G*C*T*G*T*T*T*C*C*T*G* 6, where * indicates a racemic MeP(O) linkage between 5' and 3' ends on adjoining bases, was synthesized on an Applied Biosystems DNA synthesizer, using the appropriate methylphosphoramidites. The trityl-on neutral oligonucleotide was purified by reverse-phase HPLC, then the trityl group was removed with 80% aqueous acetic acid (300 uL). The trityl-off neutral probe was purified by gel electrophoresis (50 mM histidine, pH 7.6, 300 v). Probe 6 was then 5'-end labeled using $^{32}$P ATP (Amersham) and polynucleotide kinase (Pharmacia) at 37° C. for 30 minutes. The probe was reconstituted into 50% formamide (500 uL), and was applied in 10 uL aliquots onto 1 cm ID Celquat-L200 treated filters. After 30 seconds, the filters were washed with STE buffer (1 mL). Scintillation counting of the filters showed that 0.97% of the total radioactivity remains on the filter discs.

Example 6

Nearly neutral DNA probe 6 was used to assay for M13 DNA in the ion capture format of this invention. Single-stranded template DNA target (M13mp18, New England Biolabs 404C) and control DNA (φX 174, BRL, 52645A) were diluted in 3M phosphate pH 6.8 to give final DNA concentrations of 15 pmol in 25 uL of solution. Then, kinased probe 6 solutions were added to the DNA aliquots. The solutions were then boiled for five minutes, then were cooled to 47° C. Incubation for five hours was followed by a cooling quench in ice water until processing of individual samples could commence. The hybridization solutions were applied to 1 cm ID circles of Celquat L-200 treated fiberglass discs, and were washed with 1 mL of STE, pH 7.8, with 0.02% $NaN_3$. The discs were then assayed for residual radioactivity in a scintillation counter. It was observed that counts on the probe 6/M13 filter were 30% higher than those on the filter with only probe 6. This result shows that target DNA of any sequence can be assayed for using the appropriate racemic methylphosphonate probe in an ion capture format.

Example 7

Nearly-neutral probe 6 (Example 5) can be used to assay for M13 DNA in an ion capture format of this invention. Single-stranded template DNA target (M13mp18, N.E. Biolabs) and control DNA (φX174, Bethesda Research Labs.) is diluted in buffer (30 mM NaCl, 10 mM TRIS, 10 mM $MgCL_2$, pH 8.0) to give final DNA concentrations of 1 to 100 pmole in 25 uL of solution. Kinased 6 solutions are added to the DNA aliquots to give a final volume of 50 uL. The solutions are boiled for two minutes, then cooled to 45° C. Incubation for 16 hours is followed by a cooling quench in ice water. The hybridization solutions are applied to individual wells of a 96-well microtiter plate the wells of which are coated with 0.1% polylysine (100-mer, Sigma, St. Louis, Mo.). The hybridization mixtures are incubated in the wells at 22° C. for 30 minutes, then the microtiter plate is washed with buffer. The wells can be separated, and can be counted for radioactivity by liquid scintillation counting to establish whether any target DNA has been captured.

Example 8

Nearly-neutral probe 6 can be used to assay for M13 DNA essentially as described in example 7. The probe is not kinased, however, but is conjugated to alkaline phosphatase using standard techniques. The dilution and hybridization buffers contained 0.1% BSA. The probe-template mixture is not boiled prior to hybridization, but is merely incubated at 45° C. for 16 hours. The solutions are added to treated microtiter plates, incubated, and washed as described in example 7. Instead of separating the wells and counting for radioactivity, to each well in the intact plate is added a solution containing dinitrophenylphosphate. After incubation for 15 minutes at 22° C., an aliquot of 1M $H_2SO_4$ is added, and the color in each well can be determined by spectrophotometry to establish whether any target DNA has been captured.

Example 9

This example describes the use of this invention in a kit format. The serum sample which contains the DNA of interest is first lysed with proteinase K to destroy the polyanionic proteins which may compete with the DNA for sites on the cationic fiberglass filters. Then, labeled neutral probe is added. After hybridization of probe to the target is complete, the sample is passed through a cationically charged filter. The filter is then washed with STE. After filtration, labeled DNA probe can be assayed for on the filter using appropriate techniques. If solution phase assays are desired, one can treat the filter-disc bound DNA-probe duplex with 2M aqueous piperidine, followed by another wash step. The piperidine treatment cleaves the neutral probe backbone, and the wash step will give a solution of the label.

Example 10

This example details the synthesis of nucleotide triphosphates which possess a chiral methylphosphonate group on the alpha phosphorus of the triphosphate. Treatment of the necessary four chiral P-methyl triphosphates with DNA polymerase in the presence of a template afforded the complementary probe strands that possessed chiral methylphosphonate backbones. The synthesis of alpha $P_S$- and $P_R$-methyl thymidine triphosphate will be described. The syntheses of the alpha $P_S$- and $P_R$-methyl ATP, CTP, and GTP were done in a similar fashion. To a 1M solution of 3'-O-acetylthymidine in pyridine was added 3.0 equivalents of $MeP(O)Cl_2$. After one and one-half hours of stirring at room temperature, 9.0 equivalents of 4-nitro-phenol was added. The R and S enantiomers were separated by HPLC on a silica gel column, using a linear gradient of 0.5 to 10% MeOH in $CHCl_3$. Absolute configuration at phosphorus of the individual enantiomers was established by deprotection of the 3'-acetoxy group by base, followed by in situ cyclization to give the cyclic 3',5'-methanephosphonates ($cTMP_{CH_3}$), the configurations of which are known. The resolved enantiomers were treated with diphosphate anion to give the triphosphates in dioxane/THF.

The examples above merely illustrate preferred ways of practicing this invention, but the broadest aspects of the invention are not limited to these examples. The invention is defined by the claims which follow.

What is claimed is:

1. An assay for detecting the presence or quantity of a first oligonucleotide sequence in a sample, comprising:

introducing into the sample a second oligonucleotide probe having a sequence which can hybridize with said first oligonucleotide sequence, said second oligonucleotide probe comprising a sufficient percentage of alkyl phosphonate nucleotides so that said second oligonucleotide is substantially neutrally charged, so that said first and second sequences hybridize, wherein said second oligonucleotide probe is labeled with a detectable label;

separating any unhybridized second oligonucleotide probe from said hybridized second oligonucleotide probe by contacting said sample with a positively charged solid phase so that the hybridized oligonucleotide will be retained by said solid phase, substantially without retaining unhybridized, second oligonucleotide probe; and analyzing the solid phase for the presence of said detectable label to determine the presence or quantity of said first sequence in said sample.

2. The assay as recited in claim 1 wherein said detectable label is selected from the group consisting of a radioactive label, a chemiluminescent compound, a fluorescent compound, an enzyme, biotin and a liposome containing a detectable label.

3. The assay as recited in claim 1 wherein said second oligonucleotide sequence is selected from the group consisting og chirally resolved nucleotides.

4. The assay as recited in claim 1 wherein said charged solid phase is a porous material.

5. The assay as recited in claim 1 wherein said alkyl phosphonate nucleotides are selected from the group consisting of methylphosphonate, ethylphosphonate, methylthiophosphonate and methoxyphosphonate.

6. The assay as recited in claim 1 wherein said neutrally charged oligonucleotide comprises substantially R stereoisomers of alkyl phosphonate nucleotides.

7. The method of claim 1 wherein said second oligonucleotide probe is 6 or more nucleotides in length.

8. The method of claim 1 wherein said alkyl phosphonate nucleotides are selected from the group consisting of: methylphosphonate nucleotides, ethylphosphonate nucleotides, methylthiophosphonate nucleotides, and methoxyphosphonate nucleotides.

9. The assay as recited in claim 4 wherein said porous material is coated with a positively charged material.

10. The assay as recited in claim 9 wherein said positively charged material includes a quaternary ammonium salt.

11. A kit for analyzing a sample for the presence of a first oligonucleotide sequence, comprising:

a) a positively charged solid phase; and b) a second oligonucleotide probe comprising a sufficient percentage of alkyl phosphonate nucleotides so that said second oligonucleotide is substantially neutrally charged said second oligonucleotide probe having a sequence which can hybridize with said first oligonucleotide sequence, characterized in that said second oligonucleotide probe bears a detectable label.

12. The kit of claim 10 wherein said alkyl phosphonate nucleotides are chirally resolved.

13. The kit of claim 11 wherein said label is selected from the group consisting of a radioactive label, a chemiluminescent compound, a fluorescent compound, an enzyme, biotin and a liposome containing a detectable label.

14. The kit of claim 11 wherein said solid phase is porous.

15. The kit of claim 11 wherein said solid phase is porous, and is coated with a positively charged material.

16. The kit of claim 11 further including a proteinase for digestion of any protein in the sample.

17. The kit of claim 11 wherein said second oligonucleotide is in solution.

18. The kit of claim 11 further including a wash solution to separate any unhybridized second oligonucleotide from hybridized second oligonucleotide.

19. The kit of claim W wherein said alkyl phosphonate nucleotides are selected from the group consisting of: methylphosphonate nucleotides, ethylphosphonate nucleotides, methylthiophosphonate nucleotides, and methoxyphosphonate nucleotides.

20. The kit of claim 11 wherein said second oligonucleotide probe is 6 or more nucleotides in length.

21. The kit of claim 12 wherein said nucleotides are selected from R steroisomers.

22. The kit of claim 15 wherein said positively charged material includes a quaternary ammonium salt.

23. An assay method for detecting the presence or quantity of a target oligonucleotide in a sample, comprising:
  a) introducing into the sample under hybridizing conditions, a probe oligonucleotide which can hybridize with said target oligonucleotide, said probe oligonucleotide comprising a detectable label and a sufficient percentage of alkyl phosphonate nucleotides so as to be substantially neutrally charged, whereby in the presence of said target oligonucleotide, a hybridized duplex is formed of said probe and target oligonucleotides;
  b) separating any unhybridized probe oligonucleotide from duplexes by contacting said sample with a positively charged solid phase which binds and retains said duplexes, substantially without retaining unhybridized neutral probe oligonucleotides; and
  c) analyzing the solid phase for said detectable label to determine the presence or quantity of target oligonucleotide in said sample.

24. The method of claim 23 wherein said alkyl phosphonate nucleotides are chirally resolved.

25. The method of claim 23 wherein said second oligonucleotide probe is 6 or more nucleotides in length.

26. The method of claim 24 wherein said alkyl phosphonate nucleotides are R stereoisomers.

27. A kit for detecting a target oligonucleotide in a sample, comprising:
  a) a positively charged solid phase; and
  b) a probe oligonucleotide which can hybridize with said target oligonucleotide, characterized in that said probe oligonucleotide bears a detectable label and has a sufficient percentage of alkyl phosphonate nucleotides so as to be substantially neutrally charged.

28. The kit of claim 27 wherein said solid phase comprises a quaternary ammonium salt.

29. The method of claim 27 wherein said second oligonucleotide probe is 6 or more nucleotides in length.

* * * * *

UNITED STATES PATENT AND TRADEMARK OFFICE
CERTIFICATE OF CORRECTION

PATENT NO. : 5,932,413
DATED : August 3, 1999
INVENTOR(S) : Joseph Eugene Celebuski It is certified that error appears in the above-identified patent and that said Letters Patent is hereby corrected as shown below:

Column 8,
Line 33, replace "consisting og chirally" with -- consisting of chirally resolved --.

Column 9,
Line 12, replace "kit of claim W wherein said" with -- kit of claim 11 wherein said --.

Signed and Sealed this

Fourteenth Day of May, 2002

Attest:

Attesting Officer

JAMES E. ROGAN
Director of the United States Patent and Trademark Office